(12) United States Patent  
Wyatt

(10) Patent No.: US 6,778,912 B2  
(45) Date of Patent: Aug. 17, 2004

(54) DEVICE AND METHOD TO LOCATE, DETECT, AND REMOVE PRECIPITATED AEROSOL PARTICLES

(75) Inventor: Philip J. Wyatt, Santa Barbara, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 66 days.

(21) Appl. No.: 10/279,707

(22) Filed: Oct. 23, 2002

(65) Prior Publication Data

US 2004/0083064 A1 Apr. 29, 2004

Related U.S. Application Data

(63) Continuation-in-part of application No. 09/577,108, filed on May 23, 2000, now Pat. No. 6,490,530.

(51) Int. Cl.[7] .......................... G06F 19/00; G01N 21/00
(52) U.S. Cl. ......................... 702/28; 356/337; 702/26; 702/27
(58) Field of Search ............................. 702/22, 23, 24, 702/25, 26, 27, 28, 29, 30; 356/300, 301, 335, 336, 337, 244

(56) References Cited

U.S. PATENT DOCUMENTS

| | | | | |
|---|---|---|---|---|
| 4,710,025 A | * | 12/1987 | Wyatt et al. ................ 356/343 |
| 6,184,517 B1 | * | 2/2001 | Sawada et al. .......... 250/222.2 |
| 6,407,813 B1 | * | 6/2002 | Lovette et al. ............. 356/338 |
| 6,421,121 B1 | * | 7/2002 | Haavig et al. ............. 356/338 |
| 6,490,530 B1 | * | 12/2002 | Wyatt .......................... 702/24 |
| 6,639,671 B1 | * | 10/2003 | Liu ............................. 356/336 |
| 6,639,672 B2 | * | 10/2003 | Haavig et al. ............. 356/338 |
| 2003/0144800 A1 | * | 7/2003 | Davis et al. .................. 702/22 |

OTHER PUBLICATIONS

Philip J. Wyatt and Christian Jackson, "Discrimination of Phytoplankton via Light–Scattering Properties," Limnology & Oceanography, vol. 34, pp. 96–112 (1989).

* cited by examiner

Primary Examiner—Patrick Assouad
(74) Attorney, Agent, or Firm—Philip J. Wyatt

(57) ABSTRACT

A method and apparatus are described by which previously identified aerosol particles that may have precipitated onto surfaces and/or into specific physical regions are detected, removed from said regions, and stored for later examination or destruction. The method includes means such as an ultrasonic probe to loosen said aerosol particles from the surfaces to which they have precipitated and then withdraw them into an optical read head for measurement. The optical read head illuminates each particle, previously diluted and entrained in a sheath flow, as it passes therethrough with a fine beam of light such as produced by a laser. The scattered light produced by each such particle is collected over a range of scattering angles, converted into a digital representation for each value collected, and stored in a computer means. The collected scattered light signals from each particle are then processed to compute a set of identification values, called optical observables or OOs, for subsequent comparison with a previously stored set. The latter set corresponds to the OOs of a specific particle class sought. Once a match between the OO set of a particle detected and that of a particle sought is obtained, the apparatus provides alarm and collection means by which such particles may be stored for subsequent removal and examination and/or destruction.

26 Claims, 3 Drawing Sheets

1

DEVICE AND METHOD TO LOCATE, DETECT, AND REMOVE PRECIPITATED AEROSOL PARTICLES

RELATED PATENTS

This application is a Continuation-in-Part of U.S. patent application Ser. No. 09/577,108, filed May 23, 2000, now U.S. Pat. No. 6,490,530, which is herein incorporated by reference.

BACKGROUND OF THE INVENTION

In the Fall of 2001, following the catastrophic terrorist attacks of September 11 on the United States, a series of unprecedented events unfolded that used biological agents to kill and terrorize other elements of the population. Envelopes containing highly refined spores of the species *Bacillus anthracis,* the causative agent of anthrax, were sent through the U.S. Postal Service to a variety of locations about the Washington/New York area. Once the envelopes were opened, the spores were released and inhaled by some of the unsuspecting bystanders in the vicinity. Although the mailings resulted in several deaths from inhalation anthrax and some cutaneous infections, the extensive use of antibiotics by all who may have been exposed saved countless lives. There were other equally dangerous side effects. The contaminated sites still had the potential of releasing spores and causing further deaths and illness. Two specific sites were the U.S. Senate Hart office building and the District of Columbia Brentwood mail center. The latter site was believed to be the source for the subsequent spread of spores throughout the postal system to many parts of the East Coast.

In order to establish the actual locations within the sites that remained contaminated, extensive traditional microbiological methods were used to swab defined areas, culture the plates onto which the swabs were applied, and then to read the plates and confirm the presence of anthrax bacilli on them. Decontamination by this process was unsuccessful and the final recourse for the two referenced sites was particularly disconcerting. The job of ridding large office buildings of anthrax contamination was an unprecedented one that required largely untried and complex techniques. The Hart Building itself was pumped full of toxic chlorine dioxide gas several times to kill any residual anthrax spores. The cleanup process took over three months at a cost of over $14 million. The Brentwood mail center was sealed off and, at the time of this application, was still closed. Mail service throughout the Northeast corridor had been seriously impacted.

The anthrax incidents referenced above showed the inadequacy of current methods, techniques, and ideas for the remediation of such dangerous particles that precipitate onto surfaces or are deposited into regions difficult to access. Identification methods have been speeded up considerably for the case of such pathogenic particles by the introduction of so-called "Smart chips," yet in order to identify the collected spores, they first had to be found, suspended in a liquid carrier, and then tested for surface antigens and/or germinated. Once a particular region has been identified as the source of the targeted aerosols, its remediation presents additional challenges. If the aerosols are dangerous particles such as anthrax spores or lyophilized pathogenic bacteria, the local region is generally sterilized by a disinfectant, though for the case of bacterial spores, their resilience is often too great for all but the most toxic of such agents. After disinfection, the region must be screened for the presence of residual viable particles that may have been unaffected by the process. All of these activities require time and can be exhaustive as the efforts required to screen and clear a small region are extremely labor intensive.

A further problem unanswered concerned the source of such particles. Where did they originate? Where are the most probable locations at which residues might be found? Who is responsible for the initial dissemination of the particles and can such persons be found?

The present invention addresses the problems associated with remediating dangerous particles that may have fallen to surfaces or even be freely moving in close proximity to such regions. The invention permits the rapid characterization of the particles sought and then means to locate and remove them. It is based on the monitoring systems described in the above referenced U.S. Pat. No. 6,490,530 and provides means to find targeted particles that have precipitated onto surfaces. It also provides means to remove such particles and confirm that none remain. Finally, it provides means to track the possible perpetrators of such disseminations and/or locate evidentiary traces of the targeted and precipitated aerosols.

BRIEF DESCRIPTION OF THE INVENTION

A device and method are disclosed whereby aerosol particles affixed to and/or lying on surfaces may be found, removed from such regions, and characterized by measuring their special light scattering properties called optical observables. These optical observables are then compared against those of a targeted particle class by which means their probable identity may be confirmed. The portable, computer-controlled particle search unit includes a light scattering chamber through which laminar flow entrained particles pass through a fine laser beam one-at-a-time. The light scattering signals generated during each particle's passage through the beam are processed and compared to similarly processed sets of the targeted particles sought. Whenever a match is detected, the operator is informed by an alarm or visual display. Telecommunications between the particle search unit and a central station permit data processing back-up, modification of the particle search unit's internal processing, and alarm setting.

DETAILED DESCRIPTION OF THE INVENTION

In the U.S. Pat. No. 6,490,530, a system was described to provide early warning to a population threatened by an aerosol that had been introduced by unknown persons and was comprised of dangerous particles such as anthrax spores. In that application, a set of detector stations are placed throughout a region to be monitored continuously for unusual aerosol particles by means of making light scattering measurements on such particles one-at-a-time as they pass through a fine laser beam. These data are then processed internally by means of a preprogrammed central processing unit, CPU, and transmitted to a central station whose function it is to coordinate such information received from a plurality of detectors for purposes of providing an early warning alarm to the threatened population. The present invention uses measurement capabilities similar to the detector stations described therein, but in a completely different manner. The particle search units of the present invention differ from those of the U.S. Pat. No. 6,490,530 in that they are portable, provide special hardware to loosen and remove particles from surfaces and specific regions, are preprogrammed to detect specific particle types, and provide means to collect and physically remove targeted particles from the specific surfaces and/or regions where they are activated. By facilitating the removal of targeted particles, the particle search units of the present invention maybe used for remediation of contaminated buildings and areas as well as collecting physical evidence for evidentiary purposes.

Associated with the light scattering measurements that the particle search units will make are a set of optical observables derived from them. The concept of making light scattering measurements over a range of scattering angles from single particles as they pass through a fine beam of light one-at-a-time and then combining such measurements to form a set of optical observables, on which basis the traversing particles may be characterized individually, has been described Wyatt and Jackson in the Journal of Limnology & Oceanography, volume 34, pp 96–112 (1989). The article shows an implementation and corresponding selection of OOs to differentiate particles as being members of one of a set of ten distinct classes with a certainty exceeding 99%.

The inventive concept is best described by considering a decision to search for a specific class of particles whose OOs are previously known. Such particles may be known contaminants whose removal is required from specific locations or particles whose locations are unknown and must be found in order to define specific contamination sites.

Figure 1:
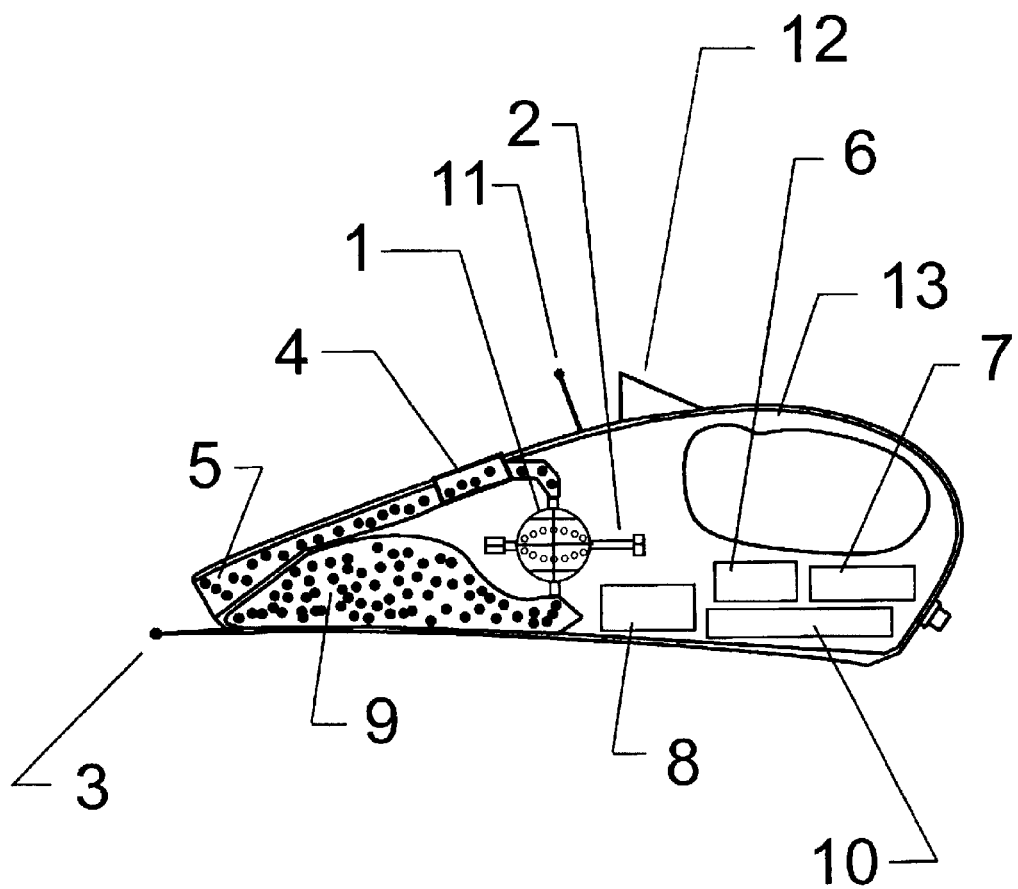
FIG. 1 presents a schematic representation of the particle search unit's key elements.

FIG. 1 presents a schematic of the particle search unit showing its remediation capabilities. The optical read head 1, shown in greater detail in FIG. 3 and the U.S. Pat. No. 6,490,530, contains light source 2 that produces a fine beam through the chamber. Generally the beam is produced by a laser such as a solid state laser. Typically beam waists of the order of 100 nm or less are used and the beam is plane polarized. For certain classes of particles, other polarizations are used to detect particles composed of optically active materials. Particles are loosened and removed from surfaces by means of an ultrasonic probe 3 placed in contact with the surface and tuned or scanned through a range of frequencies resonant with the surface material and coupled into the surface/particle interface. In operation, the tuned probe is slid along the surface while an air flow is established by the air flow module 4 to draw air with the loosened particles into the particle intake 5. In the preferred embodiment of the invention, the probe 3 would be integrated with the particle intake 5. The airflow module 4, in addition, provides for a laminar flow sheath about the particles being drawn into the optical read head 1 and dilutes the entrained particle stream to insure that particles flow through the light beam one-at-a-time. The on-board computer, CPU, and associated memory are shown at 6. A supply 7 provides power for both the computer elements 6 and associated electronics signal processing electronics 8, the latter converting the scattered light intensities to digital representations. The power supply may be self contained via a rechargeable battery or receive power from an external power source. More details of a preferred electronics configuration are shown in the U.S. Pat. No. 6,490,530. After measurement, articles are stored in the sample collection chamber 9. A telecommunications module 10 sends and receives data sets and/or programmed modifications from a central unit using antenna 11. An optional visual display 12 could be supplemented by an audible alarm controlled by the CPU 6. If the particle search unit is small and light, it may be carried by means of a handle 13.

Figure 2:
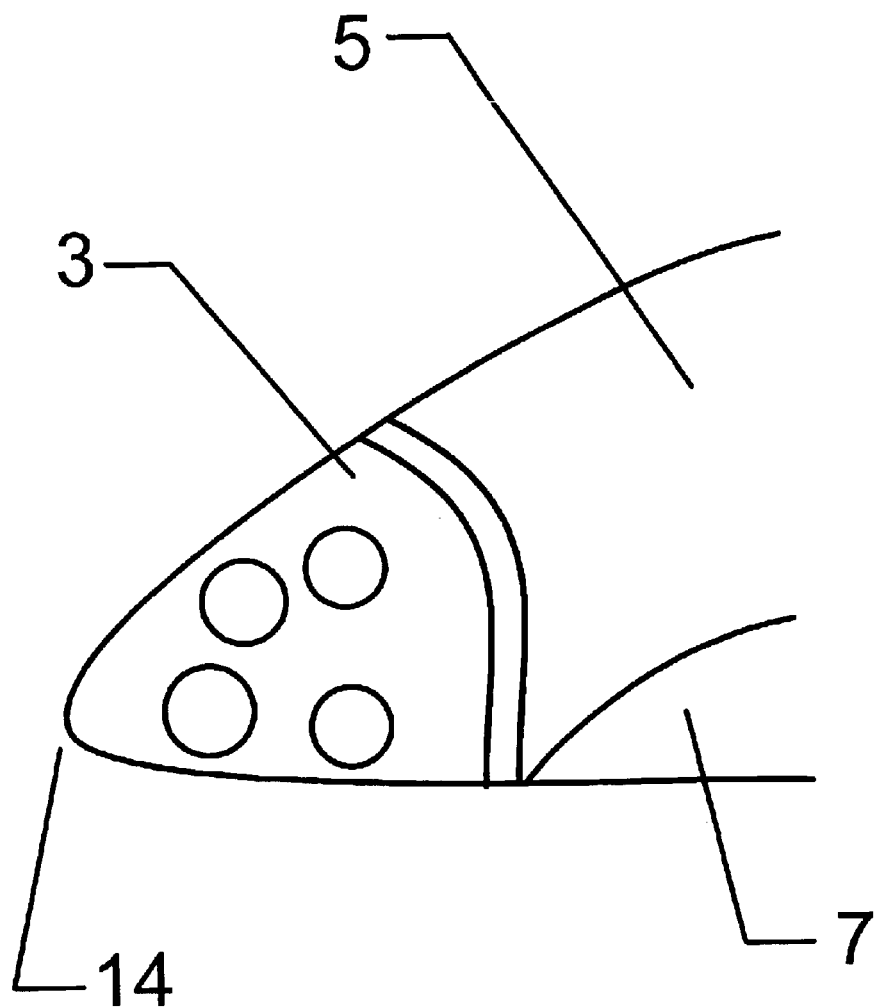
FIG. 2 shows a preferred embodiment of the ultrasonic probe.

FIG. 2 shows an integrated ultrasonic probe wherein the particle intake 5 draws in air only through perforations 14 in the probe from regions external and in close proximity to the probe 3. Part of the sample collection region 7 is also shown.

Figure 3:
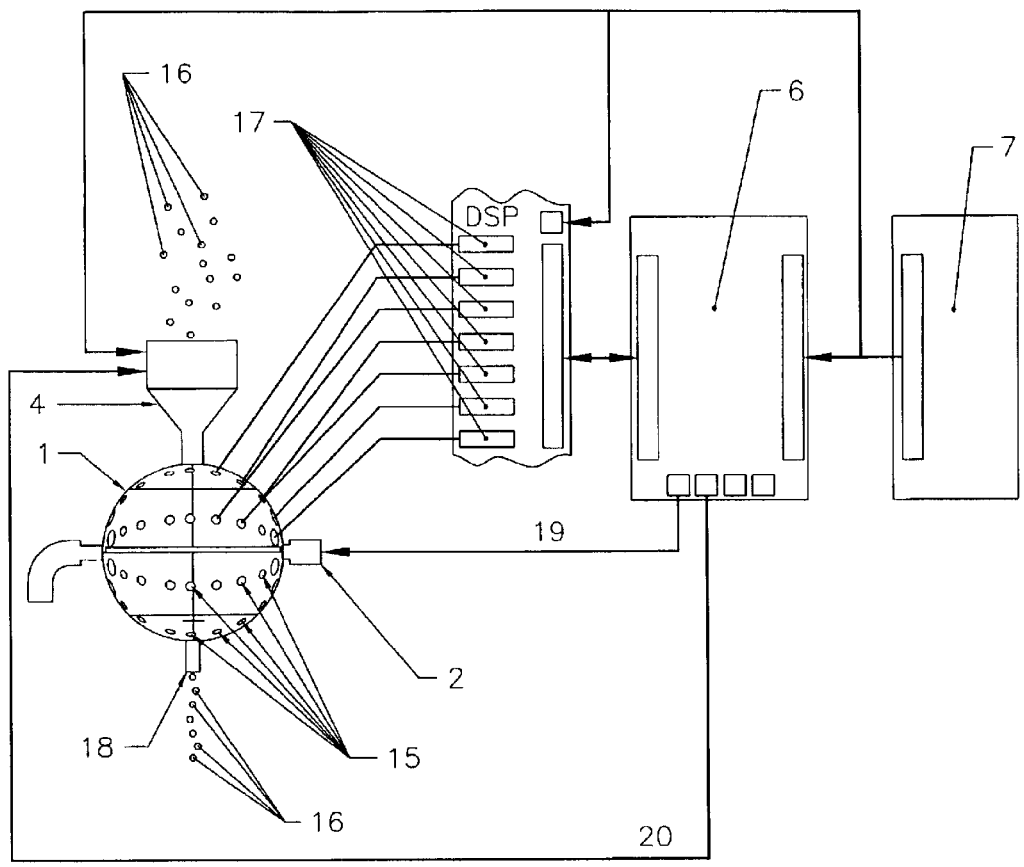
FIG. 3 is a schematic representation of the key elements of the light scattering chamber.

FIG. 3 shows the key elements of the light scattering chamber per the U.S. Pat. No. 6,490,530. The read head/scattering chamber 1 provides for the placement at 15 of scattered light detectors or optical fibers transmitting detected light thereto. Optical analyzers may be attached to said detectors or fibers the detect depolarization and other optical properties of the particles 16 drawn into the read head 1 by means of the particle intake 5 of FIG. 1. The airflow module 4 provides the means for diluting the transmitted particles 16 and entraining them in a laminar flow sheath so that they pass through the light beam one-at-a-time. The scattered light signals generated by each particle as it passes through the beam may be preprocessed by digital signal processing, DSP, chips 17. The incident light source 2 is a solid state laser in the invention's preferred embodiment such as a GaAs laser operating at a wavelength of about 685 nm. There are many other types of light sources that may find suitable implementation for the current device. In addition, more than one light source may be used in the device simultaneously. Thus a UV light source may be useful as a secondary source providing stimulus means to induce fluorescence. As the particles so measured pass out of the read head 1 through the exhaust 18, they are either discarded or collected in the sample collection chamber 9 of FIG 1. Depending upon the degree of sophistication of the sample collection elements, the system may include sorting electronics whereby only particles classified as targeted particles would be collected with all others returned to the region external to the particle search unit. Selective sorting of aerosol particles based upon previously measured optical properties is a technique well known to those skilled in the art of particle sorting. Thus particles whose OOs provide a match might be charged as they exit the exhaust 18 and then deflected my electrical means into the sample collection chamber 9. Electrical power sources to control the laser power and the airflow module are shown at 19 and 20, respectively. The CPU 6 and all other electrical elements receive power from a central power source 7.

There are means other than ultrasonic by which particles may be loosened from surfaces that may be provided by modified probe means. These include, but are not limited to short bursts of air, heating, applying electric fields, cooling rapidly, etc. The probe structure 3 may be modified to include any or several such concepts without departing from the concept of the invention.

Once particles have been released and drawn through the read head, their scattered light intensities are detected, converted into digital format, and stored in the computer means 6 for subsequent processing and analyses. Before storage, signals may be preprocessed by means of DSP chips 17.

As has been described in the preceding explanation of the figures, the inventive apparatus is comprised of nine basic elements or variations thereof:

1) mechanical means to remove particles from the interrogated surface/region, such as an ultrasonic probe;

2) air sampling means to draw such released particles into the apparatus, provide suitable dilutions of the particles to be examined and particle-free sheath flow to guide them through the 3) light scattering chamber means which provides a fine light beam, such as a laser, that intersects the flow of laminar flow entrained particles and scatters light therefrom;

4) a set of detector means collecting said scattered light at a selected set of scattering angles and including analyzing means by which depolarization of said scattered light may be quantified;

5) conversion means by which said scattered light intensities detected by said detectors are converted into digital representations and stored in 6) memory means wherein said converted light scattering intensities are stored and processed by 7) computer means capable of calculating the OOs of said corresponding scattering particles and comparing said sets with those previously defined or stored in said memory means;

8) telecommunications means by which said previously defined comparison set of OOs has been transferred into said memory means and by which means the results of analyses performed by said computer means on said sets of OOs may be transmitted to a central station or controller means; said controller means capable of modifying analytical software used by said computer means; and 9) physical storage means wherein particles whose OOs correspond to the reference set or sets stored in said memory means are collected.

In summary, therefore, the OOs of a particular target set of particles are stored in the particle search unit's memory means either transmitted thereto by telemetry means or directly through any suitable data interface. The particle search unit, which is portable and handheld in its preferred embodiment, is brought to the regions/surfaces to be interrogated for the presence of particles whose OOs match those stored in said memory means. The detection module is activated to release particles from the interrogated surface as the probe is drawn across said surface. Once released, the particles are diluted as necessary, entrained with a laminar flow sheath, and drawn into the light scattering chamber one-particle-at-a-time. As each particle passes through the light beam, its collected scattered light signals are used to generate its individual OOs which is compared with the OOs of the specific particles sought. Upon obtaining an OO match, the particle search unit is programmed to generate an audible alarm, display the result on an instrument display panel, and/or transmit the results of the OO comparison to a central station. The degree to which the measured OOs match the OOs of the specific particles sought is determined by preprogrammed computer means. Additionally, each particle search unit can transmit the unprocessed or processed data directly to a central station where the analyses are refined and completed. The central station can then instruct the particle search unit to activate an immediate alarm as well as provide it instructions to modify onboard processing of collected data. The particle search unit retains all measured particles or just those classified as targeted for subsequent physical examination.

It should be appreciated by those skilled in the art of aerosol science that the present invention fulfills a long needed means to recover aerosol particles that have fallen out of their suspending atmosphere. Although this disclosure has focused upon the preferred embodiments of such a device, there are many variants on the methods and apparatus presented that will represent obvious variations of the fundamentals presented. Such variants are included within the scope of this disclosure and claimed therewith.

I claim:

1. A particle search unit comprised of

A) a mechanical means to release particles from interrogated surfaces onto which they are believed to have settled;

B) an air sampling means to
   1. draw such released particles into said particle search unit,
   2. dilute such particles for subsequent single particle examination, and
   3. provide particle-free sheath flow to entrain and guide such particles through C) a light scattering chamber means that includes a fine light beam intersecting the flow of said sheath flow entrained particles and scattering light therefrom as they pass therethrough one-at-a-time following said dilution;

D) a set of detector means collecting said scattered light at a selected set of scattering angles and including analyzing means by which depolarizing properties of said scattered light may be quantified;

E) conversion means by which said scattered light intensities detected by said detectors are converted into digital representations and stored in F) a memory means wherein said converted light scattering intensities are stored for subsequent processing by G) a computer means capable of calculating a set of optical observables, OOs, from said converted light scattering intensities of said scattering particles and comparing said sets with those previously defined or stored in said memory means;

H) computer input/output means by which said previously defined set of OOs may be transferred into said memory means and by which means the results of analyses performed by said computer means on said sets of OOs may be transferred to a central station or controller means; said controller means capable of modifying analytical software used by said computer measuring said input/output means; and I) physical storage means wherein selected particles are accumulated and stored.

2. The particle search unit of claim 1 where said fine light beam is from a laser.

3. The particle search unit of claim 1 where said computer input/output interface is provided by telecommunications means.

4. The particle search unit of claim 1 where said mechanical means to release particles is provided by an ultrasonic probe.

5. The particle search unit of claim 1 where said mechanical means to release particles is provided by a jet of air.

6. The particle search unit of claim 1 where said mechanical means to release particles is provided by electrical means.

7. The particle search unit of claim 2 where said fine laser beam is plane polarized.

8. A method to search for and remove previously targeted particles that may have precipitated onto surfaces or into specific regions comprising the steps of A) releasing said particles by mechanical means from surfaces or specific regions selected for examination to which they are believed to have settled;

B) drawing and diluting said released particles by air sampling means through transport means;

C) providing particle-free sheath flow to entrain and guide such particles into a light scattering chamber means containing a fine light beam intersecting the flow of said sheath flow entrained particles D) scattering light from each such particle as each passes through said fine light beam one-at-a-time following said dilution;

E) collecting said scattered light by a set of detector means located at a selected set of scattering angles;

F) using analyzing means to detect from said scattered light depolarizing effects of said particles;

G) converting said scattered light intensities detected by said detectors into digital representations;

H) storing said digital representations in memory means wherein said converted light scattering intensities are stored;

I) processing said converted light scattering intensities by computer means that calculates a set of optical observables, OOs, from said converted scattered light intensities from said scattering particles;

J) comparing said sets with a set previously stored in said memory means that corresponds to said class of targeted particles sought;

K) storing said particles matching said OO properties of said sought particle class in storage means.

9. The method of claim 8 where said mechanical means for releasing targeted particles is provided by an ultrasonic probe.

10. The method of claim 8 where said mechanical means for releasing targeted particles is provided by a jet of air.

11. The method of claim 8 where said mechanical means for releasing targeted particles is provided by electrical means.

12. The method of claim 8 where said fine light beam is produced by a laser means.

13. The particle search unit of claim 1 where said conversions of said detected scattered light intensities into digital representations is performed by digital signal processing means.

14. The particle search unit of claim 1 where means to provide power for said unit is comprised of on-board battery means.

15. The particle search unit of claim 1 where said unit is portable.

16. The particle search unit of claim 1 where said input/output interface is accessible by telemetry means.

17. The particle search unit of claim 1 where said search unit is programmed to generate an audible alarm upon obtaining an OO match.

18. The particle search unit of claim 1 where said search unit is programmed to display the result on an instrument display panel upon obtaining an OO match.

19. The particle search unit of claim 1 where said search unit is programmed to transmit the results of an OO match to a central station.

20. The particle search unit of claim 2 where said laser beam is plane polarized.

21. The particle search unit of claim 2 where said laser is a GaAs laser operating at a wavelength of about 685 nm.

22. The method of claim 8 where said conversions of said detected scattered light intensities into digital representations is performed by digital signal processing means.

23. The method of claim 8 where said storage into storage means of said particles matching said OO properties of said sought particle class is controlled by sorting electronics means.

24. The method of claim 8 where said memory means is accessible by an input/output interface means.

25. The method of claim 12 where said laser beam is plane polarized.

26. The method of claim 12 where said laser is a GaAs laser operating at a wavelength of about 685 nm.

* * * * *